(12) United States Patent
Mehta

(10) Patent No.: US 10,758,587 B2
(45) Date of Patent: *Sep. 1, 2020

(54) FORMULATIONS FOR THE TREATMENT OF DISORDERS OF THE MOUTH, THROAT AND RESPIRATORY TRACT

(71) Applicant: Raman Mehta, Kowloon (HK)

(72) Inventor: Raman Mehta, Kowloon (HK)

( * ) Notice: Subject to any disclaimer, the term of this patent is extended or adjusted under 35 U.S.C. 154(b) by 381 days.

This patent is subject to a terminal disclaimer.

(21) Appl. No.: 15/735,361

(22) PCT Filed: Jun. 10, 2016

(86) PCT No.: PCT/IB2016/000795
§ 371 (c)(1),
(2) Date: Dec. 11, 2017

(87) PCT Pub. No.: WO2016/198943
PCT Pub. Date: Dec. 15, 2016

(65) Prior Publication Data
US 2018/0169175 A1    Jun. 21, 2018

(30) Foreign Application Priority Data

Jun. 10, 2015  (EP) .................................... 15171354

(51) Int. Cl.
| | | |
|---|---|---|
| *A61K 36/9066* | (2006.01) | |
| *A61K 36/9068* | (2006.01) | |
| *A61K 36/185* | (2006.01) | |
| *A61K 9/00* | (2006.01) | |
| *A61P 1/02* | (2006.01) | |
| *A61P 11/04* | (2006.01) | |
| *A61P 11/02* | (2006.01) | |

(52) U.S. Cl.
CPC ........ *A61K 36/9066* (2013.01); *A61K 9/0056* (2013.01); *A61K 36/185* (2013.01); *A61K 36/9068* (2013.01); *A61P 1/02* (2018.01); *A61P 11/02* (2018.01); *A61P 11/04* (2018.01); *A61K 2300/00* (2013.01)

(58) Field of Classification Search
None
See application file for complete search history.

(56) References Cited

U.S. PATENT DOCUMENTS

2009/0175971 A1   7/2009  Dreher
2012/0107429 A1   5/2012  Lee et al.

FOREIGN PATENT DOCUMENTS

| CN | 102670588 A | 9/2012 |
| CN | 103638502 A | 3/2014 |
| CN | 104524508 A | 4/2015 |
| DE | 202009002126 U1 | 4/2009 |
| JP | 2004537575 A | 12/2004 |
| JP | 2013539770 A | 10/2013 |
| WO | 2011068812 A1 | 6/2011 |

OTHER PUBLICATIONS

U.S. Appl. No. 15/735,391, filed Dec. 2017, Mehta; Raman.*
JP2013001666A English translation retrieved from https://worldwide.espacenet.com/. (Year: 2013).*
Ahmad et al., "Bioactive Compounds from Punica Granatum, Curcuma Longa and Zingiber Officinale and their Therapeutic Potential," Drugs of the Future, vol. 33, No. 4, Apr. 1, 2008, pp. 329-346.
Database WPI, Week 201308, Thomson Scientific, XP-002748586, London, Jan. 7, 2013.
International Search Report issued on PCT/IB2016/000795 dated Aug. 18, 2016.
Soheil Z. Moghadamtousi et al., "A Review on Antibacterial, Antiviral, and Antifungal Activity of Curcumin," BioMed Research International, vol. 2014, 12 pages.

* cited by examiner

*Primary Examiner* — Michael Barker
(74) *Attorney, Agent, or Firm* — Carter, Deluca & Farrell LLP

(57) ABSTRACT

The present invention relates to formulations containing a combination of extracts from *Curcuma longa*, *Punica granatum* and *Zingiber officinale*, acting synergistically in the treatment and prevention of disorders of the mouth, throat and respiratory tract; the formulation is especially active on disorders of bacterial origin, e.g. those occurring in patients affected by common cold and flu and their complications. The present formulations are particularly useful in the reduction of incidence of sores throat and their infections and in the elimination of antibiotic use, especially among infants and the elderly.

12 Claims, No Drawings

FORMULATIONS FOR THE TREATMENT OF DISORDERS OF THE MOUTH, THROAT AND RESPIRATORY TRACT

CROSS REFERENCE TO RELATED APPLICATIONS

This application is a national stage application of International Application No. PCT/IB2016/000795, filed Jun. 10, 2016, which claims the benefit of and priority to European Patent Application No. 15171354.2, filed Jun. 10, 2015, the entire contents of each of which are hereby incorporated by reference herein.

STATE OF THE ART

Inflammation and bacterial infection of the throat with plaque formation are symptoms that accompany common influenza, cold and winter diseases. The common cold is generally considered the most common human disease, affecting people in all countries and social contexts. Adults may have two to five colds every year, particularly in crowded communities and in winter; children in contact with other children may have six to ten cold episodes every year, with up to twelve colds/year for kindergarten or school children. (1-10) However, some episodes may be minimally symptomatic.

The common cold and flu are viral diseases localized in the upper respiratory tract; responsible of the infection are generally for 40% rhinovirus, for 10% coronavirus and in minor proportion adenovirus, parainfluenza virus followed by bacterial infection. (1-6) Cold episodes may be associated with symptoms such as nasopharyngitis, rhinopharyngitis, increase in temperature, ear and throat complications and respiratory problems. Common symptoms may include cough (usually a few days after the onset), sore throat, runny nose and fever. Symptoms disappear in five to ten days. In some cases, particularly in older, higher-risk subjects, residual symptoms may last up to three weeks. The frequency of common cold episodes tends to increase in older subjects and in patients at risk, mainly due to a deterioration of the immune system. Influenza is particularly dangerous in the elderly due to the frequent serious and debilitating complications, leading at serious risk of death.

In industrialized countries, particularly in crowded communities, 30% of the population may be affected every winter. The costs due to lost working hours, medications, complications and altered social interactions are significant. An effective vaccine is not available as many different viruses (which also change over time) are involved. Hand cleaning and washing may reduce the exchange of viruses. Aspirin, supplements, particularly vitamin C and zinc, may be effective in decreasing the rate of colds and the length of each episode. (4-8) Analgesics and antipyretics may alleviate specific symptoms. (9-16) Decongestants (i.e., pseudoephedrine, ipratropium and other nasal spray) may reduce the symptoms of a runny nose. The symptoms associated with a runny nose may be controlled by antihistamines but these products may cause significant adverse reactions such as drowsiness, impaired attention and driving performance. The cold disorders sometimes involve complications due to the onset of bacterial infections causing fever and pain. In these cases antibiotic or bacteriostatic treatment is necessary in addition to the symptomatic treatment. Antibiotics are lowering the body's defenses giving rise to frequent relapses particularly in children. Cough and cold medications in children (<6 years) generally are not advised as they may cause significant side effects and complications and provide unproven benefits. About 30% of older patients may develop complications (upper respiratory tract infection, bronchitis, pneumonia). In high-risk subjects (severe risk conditions, heavy smokers, diabetics, handicapped subjects, patients with previous, chronic cardiovascular or pulmonary problems), complications may be severe and cause hospital admission with increasing social/human costs.

At the moment no specific treatment or prevention for colds is available. New products with good tolerability to be used also in prevention are today very requested.

Various plant remedies have been proposed for treating cold-related diseases; these natural products may have lesser toxicity than synthetic drugs, yet they often show a lesser/less consistent activity. Plant extracts and mixtures thereof are also generally proposed; sometimes, combinations of medicinal plants are also "conservatively" proposed, i.e. involving the combination of a very large number of active agents against a multitude of unrelated diseases, so as to provide a widest spectrum of activities; yet the activity of specific active agents present in the mixture against specific (groups of) diseases remains unknown: for example, the patent publication JP2013001666 describes a nutrient composition for treating a variety of conditions including atherosclerosis, cancer, cell damage, diabetes, cranial never disease, cerebral infarction, dementia, parkinson's disease, alimentary mucosa disease, lung/bronchus disorder, inflammation, menopausal disorder, rheumatism, atopic disease, containing inter alia, curcuma longa extract (used in lower ratios than in the present invention), silylbum marianum seed, emblica officinalis extract, wheat bran, Japanese tea leaf extract, sesame extract, pomegranate seed extract, ginger extract, soy isoflavone, withaniaroot, bacopa monnierileaf, etc. Other publications disclose compositions for a narrower medical indication, but fail to individualize the combination of agents on which the present invention is based. For example, the utility model DE 20 2009 002 126 describes a nutritive composition useful for treating subjects under chemo-/radiotherapy: the composition contains a multitude of vitamins, minerals, carotenoids, omega-3-fatty acids, pomegranate extract and at least one extract chosen from broccoli, ginger and curcuma; in the exemplified compositions, the active ingredients of the present invention represent a minority part of the total active ingredients present. The patent application WO-A1-2011/068812 describes compositions for treating the oral cavity containing at least three of Punica granatum, Myristica fragrans, Zingiber officinale and Zizyphus joazeiro, and an additional extract selected from another 38 plants; there is no specific disclosure of the combination on which the present invention is based.

The publication Drugs of the Future, 2008, 33(4), pp. 329-346 describes separately the activities of Punica granatum, Curcuma longa or Zingiber officinale: the document describes the general biochemical effects of these plants and their active components (antioxidant, anti-inflammatory, antimicrobial, anticancer, antimutagenic), with no suggestion or teaching on how to optimize their activities; the document does not suggest any specific combination of these agents, nor it prospects a possible synergism among them.

Very little research was so far performed in identifying specific combinations of more than two extracts: in particular, no guidance is given to identify specific combinations possibly capable to offer more than just overalapping effects in the pathologies of the mouth, throat and respiratory tract.

SUMMARY

It has now been discovered that a combination of extracts of *Curcuma longa, Punica granatum* and *Zingiber officinale* displays a strong synergistic activity on disorders of the mouth, throat and respiratory tract; this activity, involving a strong antimicrobial effect, is particularly useful against affections occurring during common cold and flu. Objects of the invention are the aforesaid combination of extracts, the relevant pharmaceutical compositions, methods of preparation, and use thereof in the treatment/prevention of disorders of the mouth, throat and respiratory tract. In particular, the invention encompasses the aforesaid combination of extracts for use in the treatment/prevention of said disorders, and the corresponding methods of treatment.

DETAILED DESCRIPTION OF THE INVENTION

*Curcuma longa* is the botanic name of turmeric. *Punica granatum* is the botanic name of pomegranate. *Zingiber officinale* is the botanic name of *ginger*. For each of these plants, the botanic and common name are used herein indifferently.

Throughout this description and claims, whenever weight (or weight percent) amounts of extracts are disclosed, they are always meant as "dry" extracts, i.e. considering only the weight of the non-liquid ingredients of the extract; likewise, whenever weight (or weight percent) amounts of specific ingredients within an extract are disclosed, they are always calculated by reference to the extract in "dry" form.

Nevertheless, the combinations/formulations/pharmaceutical compositions/uses objects of the present invention are not limited to using dried extracts, but extend also to using liquid and fluid extracts. Any types of extracts can be used herein, indifferently from their specific method of extraction and their physical status.

*Curcuma longa* extracts are usually obtained from roots and rhizomes of the plant. They contain curcuminoids in association with other plant components working as natural vehicles. Total alcoholic extracts are preferably used; they can be prepared e.g. according the modalities of Ayurveda system of medicine (Turmeric extract), by extraction of *Curcuma* rhyzomes with ethanol; they typically contain 20-30% wt curcuminoids, preferably 25% wt., referred to the dry extract.

*Punica granatum* extracts are typically obtained from the whole fruit. They have a polyphenol content generally ranging from 60 to 95% wt., preferably 75%; ellagic acid and polymers thereof (punicalgines) are the main active components of the extract: they are normally present in the extract in a minimum amount of 30% wt, preferably more than 40% wt., referred to the dried extract. In a preferred embodiment, the extract can be prepared by extracting the whole fruits with mixtures of ethanol/water or acetone, concentrating the extracts to water and purifying the aqueous solution, after elimination of insoluble material, through absorption of polyphenos on a polystirenic resin; the polyphenols are recovered from the resin by elution with ethanol and then concentrated to dryness.

*Zingiber officinale* extract is usually obtained from rhizomes. It is preferably a lipophilic extract; it contains from 20 to 50% of a mixture of gingerols+shoagols, referred to the dried extract. In a preferred embodiment, it is obtained by extraction of the dried rhizomes with n-Hexane or with $CO_2$ in supercritical condition at a temperature of 45° C. and a pressure of 220 bars.

In one embodiment of the invention, the three aforementioned extracts are the sole active agents used (this does not preclude the joint use of non-active agents, i.e. vehicles and formulation excipients, including those possibly having a pharmaceutical effect as a side activity: the latter may still be used in modes/amounts conform to their role as vehicle/excipient).

Alternatively, additional active agents may be used, but on condition that the combination of extracts of the invention remains prevalent, i.e:

said combination of *Curcuma longa, Punica granatum* and *Zingiber officinale* accounts for more than 50% (or, preferably, more than 75%, 85%, 90%, 95% or 99%) by weight of the total active agents present and/or any possible active agent additional to said *Curcuma longa, Punica granatum* and *Zingiber officinale* is present in an amount at least 50% by weight lower than the lowest among said *Curcuma longa, Punica granatum* and *Zingiber officinale*: accordingly a combination of, for example, 60 mg turmeric extract, 20 mg pomegranate extract and 10 mg *ginger* extract, will allow the presence of additional active agents, each one being present in amounts of 5 mg or lower.

Further in the invention, *Curcuma Longa* is generally present in higher concentrations compared to the two other members, i.e. *Zingiber Officinale* and *Punica granatum*, i.e. the weight ratio among these three active agents, based on their dried extracts, is: 6(±2):2(±1):1(±0.5), where the data in parenthesis represent possible ±weight ratio variations for each component.

According to another preferred embodiment, the formulations contain the three extracts within the following weight intervals, per dosage unit, referred to dried extracts:

| | |
|---|---|
| *Curcuma longa* extract: | 20 to 100 mg, |
| *Punica granatum* extract (ctg. 40% ellagic acid deriv.) | 10 to 60 mg |
| *Zingiber officinale* extract (ctg. 35% gingerols): | 2 to 20 mg |

According to a more preferred embodiment the content per dosage unit, referred to dried extracts, is:

| | |
|---|---|
| *Curcuma longa* extract: | 50 mg, |
| *Punica granatum* extract (ctg. 40% ellagic acid deriv.) | 20 mg |
| *Zingiber officinale* extract (ctg. 35% gingerols): | 10 mg, | each of these amounts being variable within a range of ±15%.

A further preferred embodiment concerns the slow release formulation tablet described in example 1 of this application, or the orodispersible mucoadhesive tablet described in example 2 of this application, wherein the weight of each of the formulation ingredients can vary within a range of ±15%.

Most preferably, the combination of the present invention is formulated as a buccal composition, i.e. for local application in the buccal cavity, capable to release the active principles during a prolonged time after application, typically formulated as an orodispersible tablet or film (preferably mucoadhesive); alternatively the combination is formulated as inhalatory composition, e.g. as aerosol, spray, etc. In particular the inventors have unexpectedly found that the present combination of extracts, after a suitable time of permanence in the buccal cavity ensures an increase in the amount of salivar lysozyme, an enzyme involved in capturing/inactivating possible environmental contaminants entering in the mouth such as bacteria and viruses. Even more surprisingly, the found increase was unrelated to enhanced salivation, i.e. it consisted in an enhanced salivar concentration of lysozyme, thus independent from the amount of secreted saliva. The present combination is thus unexpectedly effective when formulated as a buccal sustained release composition, exerting a very effective preventive effect against bacterial of viral infection such as common flu. The critical importance of an effective preventive treatment for these diseases is immediately evident, considering their widespread diffusion, their social impact and the length of curative therapies once infection has taken place, often involving the undesirable use of antibiotic drugs.

The daily dosage at which the present combination is administered can widely vary in function of the patient conditions, administration route, and type and severity of the disease to be treated. Said daily dosage can be taken via a single administration or, preferably, subdivided in repeated administrations throughout the day, e.g. 3 times a day. The treatment is effective almost immediately: however prolongation of the treatment over a minimum of 2-3 days, preferably for 1 or 2 weeks, is advised to obtain a significant and consistent inhibition of the symptoms.

The combination of extracts of the invention, although being effective as such, is preferably formulated and provided to the patient in a conventional delivery form suitable for administration in the mouth (oral or buccal routes) or via the respiratory tract. Preferred oral administration forms are tablets, capsules, granules, pellets, gummy lozenges, chewing gum etc.; more preferred are those formulated for a slow/controlled release; also preferred are tablets capable to form gels once in contact with water, so as to ease administration in patients with difficulties to swallow solid bodies, e.g. babies and elderly. Aerosols, sprays and similar, are also employable for a direct delivery of the formulation to the respiratory tract. All the above delivery forms can be prepared according to conventional methods as reported in standard books of Pharmaceutical technology.

The combinations and formulations of the invention proved highly active on disorders of the mouth, throat and respiratory tract, especially those of bacterial origin; in particular, they successfully prevented the formation of bacterial plaques, fever and other symptoms accompanying colds and influenza. Further disorders treatable by the present combinations and formulations are nasopharyngitis, rhynopharingitis, sore throat, cough, runny nose, increase in body temperature, ear and/or throat complications, respiratory problems, bronchitis, penumonia, sneeying, rhinorrhea, nasal obstruction, malaise, headache, and related conditions.

The main therapeutic effects are obtained by the present combination: antibacterial activity, usefully complemented by anti-inflammatory, antioxidant, and antiviral activities, as well as by an increase in the lysozime content of the saliva. Without being bound by theory, it is believed that the polyphenolic fraction of *Punica granatum* may be associated with NFkB inhibition, with useful effects on inflammation and immune response to infection; the punicalgines present in the extract may be responsible at least partly responsible for antiviral effects; *Zingiber officinale* may be responsible for antibacterial, antiviral and anti-inflammatory activities due to its inhibitory effect on NFkB and lipo-oxigenases; it also believed to produce analgesic effects due to its interaction with vanilloid receptors, TRPV1.

All the above activities advantageously and unexpectedly synergize in the present combination, providing the patient with an unexpectedly high level of protection against the above referred disorders. The presence of synergism was in fact detected not merely in vitro but in clinical trials on patients, thus certainly occurring in the clinical practice where it is actually requested. The combination also achieved a strong enhancement of lysozime levels in the saliva, up to 5 times the levels in healthy subjects: since lysozime is involved in the lysis of bacteria and other xenobiotics, this complementary effect further enhances the immunoprotective properties of the saliva, strengthening the resistance of the mucosa of the mouth and neighbouring areas against infections. The formulation was also found to build a temporary protective layer upon the contacted mucosas, thus further increasing their resistance against pathogenic agents present in the atmosphere.

EXAMPLES

Example 1

Slow Release Formulation Tablet

| | |
|---|---|
| *Curcuma longa* alcoholic extract (turmeric) or other species | 50 mg, |
| *Punica granatum* extract 40% ellagic acid der.: | 20 mg |
| *Zingiber officinale* lipophilic extract 35% gingerols: | 8 mg |
| Xylitol: | 430 mg |
| Hyaluronic acid: | 200 mg |
| Ammonium glycirrizinate | 10 mg |
| Sodium Cyclamate | 40 mg |
| Polysorbate 80 | 5 mg |

Example 2

Orodispersible Mucoadhesive Tablets

| | |
|---|---|
| *Curcuma longa* alcoholic extract (turmeric) or other species | 50 mg, |
| *Punica granatum* extract 40% ellagic acid der | 20 mg |
| *Zingiber officinale* lipophilic extract | 10 mg |
| Alginic acid Sodium salt | 200 mg |
| Xylitol | 600 mg |
| Ammonium glycirrizinate | 10 mg |
| Sodium Cyclamate | 40 mg |
| Polisorbate 80 | 5 mg |

Example 3

Clinical Trials

In the present study a large number of patients (more than 60 per group) was involved; the subjects were informed about any supplement or treatment and knew what the supplement was; a possible placebo effect was carefully explained and considered; data were analysed after the observation period, ideally when sufficient evidence had been collected; the time needed to see differences among groups was also considered an evaluation target.

As patient selection criteria, the following 7 "pillars" of cold (Merck Manual 2011) were used:
1. "Scatchy" sore throat.
2. Sneezing.
3. Rhinorrhea 4. Nasal obstruction.
5. Malaise.
6. Cough.
7. Temperature.

Signs/symptoms 1 to 5 are almost always present, while 6 and 7 may be present in some 15-20% of patients; signs/symptoms were scored by patients on a 10 cm horizontal analogue scale line (Cyril Maxwell, Clinical Research for all. Cambridge medical publications, Cambridge, 1973); patients with at least 6 out of 7 of the "cold pillar signs" were diagnosed to have a cold.

The main targets of the clinical trials were:

a—the evaluation of the occurrence of episodes
b—the reduction of signs/symptoms
c—the reduction of days of disease, the reduction in the use of other symptomatic treatments
d—the control of cold-related potential complications.
e—Determination of saliva and lysozyme content The formulation described in example 1 was administered 3 times daily allowing to slowly dissolve in the mouth; the duration of the administration period was two weeks plus an other week for observation. The study was a pilot registry study and the results and data were evaluated by an external reviewing panel not in contact with the patients. The data, tolerability and possible adverse effects were monitored daily in a diary during the whole period of treatment+observation. The results are summarized in table 1.

TABLE 1 main clinical results after 3 weeks (2 weeks of treatment + one week of observation)

|  | FORMULATION OF EXAMPLE 1 | CONTROLS |
|---|---|---|
| Protocol: 3 tabs. daily, over 14 days. No. registered patients: | 63 | 67 |
| Age(mean; SD) | 42.3; 2 | 41.4; 2 |
| Patients completing the trial | 61 | 63 |
| Drop out | 2 | 4 |
| Cold episodes in week 3 | 3 (8.1%) | 6 (26.98%) |
| Affected days (mean; SD) | 2.9; 1.1 | 4.6; 1.2 |
| Use of OTC products/treatments (on demand basis), of which: | 11/61 | 22/61 |
| Nasal drops | 10% | 34% |
| Aspirin + VitaminC | 7% | 12% |
| Antihistamines | 3% | 9% |
| Aerosols | 12% | 26% |
| Complications after 4 days of which: | 2/61 | 5/61 |
| Disease lasting >4 days | 0 | 2 |
| Tracheal affection | 1 | 1 |
| Bronchial affection | 1 | 2 |

On randomly selected patients, the lysozyme concentration in the saliva was evaluated before the first administration (controls), and after 1 week of treatment (3 tablets/daily). The results are reported in table 2.

TABLE 2

Mean values for lysozyme concentration (micrograms/ml, turbidimetric assay) in centrifuged saliva. Patient population: 10 male subjects/age range 35-55 yrs, mean 42.32; 3.4 yrs

| Patient no. | Lysozyme before administration | 1 week after administration |
|---|---|---|
| 01 | 2.3 | 2.9 |
| 02 | 2.3 | 7.5 |
| 03 | 2.4 | 12.3 |
| 04 | 2.1 | 11.2 |
| 05 | 2.0 | 12.1 |
| 06 | 2.3 | 11.4 |
| 07 | 2.4 | 12.0 |
| 08 | 2.2 | 11.8 |
| 09 | 2.4 | 13.0 |
| 10 | 2.2 | 11.4 |

To demonstrate the synergistic effect of the combination versus the single ingredients a pilot clinical trial has been carried out on 5 groups of 12 patients suffering of bacterial infection of the oral cavity; a first group was treated with a combination of extracts according to the invention (Sample D), 3 times a day for 3 days. The remaining groups of patients were administered, under the same administration protocol, either: a placebo formulation (Sample E), *Curcuma longa* extract alone (Sample A), *Punica granatum* extract alone (Sample B), or *Zingiber officinale* alone (Sample C); each of the single extracts was administered in the same amount as present in Sample D. One hour before and one hour after the last treatment the patients gargled for 30 sec with physiological solution and 0.5 mL were plated on agar for bacterial counting after incubation for 36 h according the lab standard conditions.

The results are reported in the following table 3:

TABLE 3

|  | Bacterial count ($\times 10^5$) in physiological sample | |
|---|---|---|
|  | Before treatment | After treatment |
| Sample A (*Curcuma longa*) | 46.0 | 34.5 |
| Sample B (*Punica grantatum*) | 44.0 | 39.8 |
| Sample C (*Zingiber officinale*) | 30.9 | 28.6 |
| Sample D (Combination) | 40.6 | 6.5 |
| Sample E (Placebo) | 43.0 | 44.2 |

It can be noted that the effect after treatment with Sample D according to the invention is unexpectedly higher than each of the three Samples A, B, C taken alone. The effect of Sample D is also higher compared to the cumulated effects obtained by Samples A+B+C.

REFERENCES

1. Eccles R, Weber O. Common cold (Online-August ed). Basel: Birkh. user; 2009. p. 197.
2. Gwaltney J M Jr, Halstead S B. Contagiousness of the common cold. Journal of the American Medical Association 1997;278(3).
3. Cohen S, Doyle W J, Alper C M, Janicki-Deverts D, Turner R B. Sleep habits and susceptibility to the common cold. Arch Intern Med 2009;169:62-7.
4. Lawrence D M. Gene studies shed light on rhinovirus diversity. Lancet Infect Dis 2009;9(5).
5. Jefferson T, Del Mar C B, Dooley L, Ferroni E, Al-Ansary L A, Bawazeer G A et al. Physical interventions to interrupt or reduce the spread of respiratory viruses. CADTH Technol Overy 2012;2:e2302.
6. Singh M, Das R R. Zinc for the common cold. Cochrane Database of Systematic Reviews 2007;2. (February 2011).
7. Hemil. H, Chalker E, Douglas B, Hemil. H. Vitamin C for preventing and treating the common cold. Cochrane Database of Systematic Reviews 2007;3:CD000980.
8. Simasek M, Blandino D A. Treatment of the common cold. American Family Physician 2007;75:515-20.
9. Kim S Y, Chang Y J, Cho H M, Hwang Y W, Moon Y S. Non-steroidal anti-inflammatory drugs for the common cold. Cochrane Database Syst Re 2009;3.
10. Eccles R. Efficacy and safety of over-the-counter analgesics in the treatment of common cold and flu. Journal of Clinical Pharmacy and Therapeutics 2006;31:309-19.
11. Smith S M, Schroeder K, Fahey T. Over-the-counter (OTC) medications for acute cough in children and adults in ambulatory settings. Cochrane Database Syst Rev 2012;8:CD001831.
12. Shefrin A E, Goldman R D. Use of over-the-counter cough and cold medications in children. Can Fam Physician 2009;55:1081-3.
13. Vassilev Z P, Kabadi S, Villa R. Safety and efficacy of over-the counter cough and cold medicines for use in children. Expert opinion on drug safety 2010;9:233-42.
14. Taverner D, Latte G J. Nasal decongestants for the common cold. Cochrane Database Syst Rev 2007;1.
15. Albalawi Z H, Othman S S, Alfaleh S. Intranasal ipratropium bromide for the common cold. Cochrane Database Syst Rev
16. Pratter M R. Cough and the common cold: ACCP evidence-based clinical practice guidelines. Chest 2006; 129(1 Suppl):72S-4S.
17. Guppy M P, Mickan S M, Del Mar C B, Thorning S, Rack A. Advising patients to increase fluid intake for treating acute respiratory infections. Cochrane Database Syst Rev 2011;2:CD004419.
18. Singh M, Singh M. Heated, humidified air for the common cold. Cochrane Database of Systematic Reviews 2011;5.
19. Paul I M, Beiler J S, King T S, Clapp E R, Vallati J, Berlin C M. Vapor rub, petrolatum, and no treatment for children with nocturnal cough and cold symptoms. Pediatrics 2010;126:1092-9.
20. Arroll B, Kenealy T. Antibiotics for the common cold and acute purulent rhinitis. Cochrane Database Syst Rev 2005;3.
21. Oduwole O, Meremikwu M M, Oyo-Ita A, Udoh E E. Honey for acute cough in children. Cochrane Database of Systematic Reviews 2010;1. upper respiratory tract infections. Cochrane Database of Systematic Reviews 2010; (3).
22. Kassel J C, King D, Spurling G K. Saline nasal irrigation for acute
23. Kormos W. On call. I always catch colds during the winter and they last more than a week. I heard that zinc and *echinacea* help to shorten colds. Should I try them? Hary Mens Health Watch 2012;17:2.
24. Heiner K A, Hart A M, Martin L G, Rubio-Wallace S. Examining the evidence for the use of vitamin C in the prophylaxis and treatment of the common cold. Journal of the American Academy of Nurse Practitioners 2009;21: 295-300.
25. Al-Nakib W. Prophylaxis and treatment of rhinovirus colds with zinc gluconate lozenges. J Antimicrob Chemother 1987;20:893-901.
26. Turner R B, Fowler S L, Berg K. Treatment of the common cold with troxerutin. APMIS 2004;112. 605-11.
27. Berg K, Andersen H, Owen T C. The regulation of rhinovirus infection in vitro by IL-8, HuIFN-alpha, and TNF-alpha. APMIS 2004;112:172-82.

The invention claimed is:

1. A method of preventing and/or treating disorders of the mouth, throat and respiratory tract, comprising administering to a patient in need thereof, a combination of active agents consisting of extracts of *Curcuma longa, Punica granatum* and *Zingiber officinale*, the extracts being present in the respective weight ratios 6(±2):2(±1):1(±0.5).

2. A method of preventing and/or treating disorders of the mouth, throat and respiratory tract, comprising administering to a patient in need thereof, a combination of active agents comprising extracts of *Curcuma longa, Punica granatum* and *Zingiber officinale*, the extracts being present in the respective weight ratios 6(±2):2(±1):1(±0.5),
wherein the extracts represent overall more than 50% by weight of the total administered active agents, and/or
wherein each possible active agent additional to the extracts is present in an amount at least 50% by weight lower than the lowest among the extract of *Curcuma longa, Punica granatum* and *Zingiber officinale*.

3. The method according to claim 2, wherein the extracts of *Curcuma longa, Punica granatum* and *Zingiber officinale* represent overall more than 90% by weight of the total administered active agents.

4. The method according to claim 1, wherein the extract of *Curcuma longa* contains curcuminoids in an amount from 20% to 30% by weight, the extract of *Punica granatum* contains polyphenols in an amount from 60% to 95% by weight, and the extract of *Zingiber officinale* contains a total of gingerols and shogaols in an amount from 20% to 50% by weight.

5. The method according to claim 1, wherein the combination is formulated as a unit dose of administration, comprising: 20-100 mg of *Curcuma longa* extract; 10-50 mg of *Punica granatum* extract; and 2-20 mg *Ginger officinale* extract.

6. The method according to claim 1, wherein the combination is formulated with pharmaceutical excipients.

7. The method according to claim 1, wherein the combination is in a form suitable for buccal, oral or inhalatory administration.

8. The method according to claim 1, wherein the disorder is connected with bacterial activity.

9. The method according to claim 1, wherein the disorder is consequential to common cold or flu.

10. The method according to claim 1, wherein the disorder is one or more among: nasopharyngitis, rhynopharingitis, sore throat, cough, runny nose, increase in body temperature, ear and/or throat complications, respiratory problems, bronchitis, penumonia, sneezing, rhinorrhea, nasal obstruction, malaise, headache, and related conditions.

11. The method according to claim 1, wherein the combination is configured for enhancing lysis of xenobiotics via contact of the combination with the saliva.

12. A pharmaceutical composition comprising the combination of extracts according to claim 1.

* * * * *